| United States Patent [19] | [11] Patent Number: 4,851,442 |
| Watson | [45] Date of Patent: Jul. 25, 1989 |

[54] LIDOCAINE HYDROCHLORIDE, CITRIC ACID AND DIMETHYL SULFOXIDE, SOLUTION, AND FORMATION THEREOF

[76] Inventor: W. Keith R. Watson, 2749 Via Viejas, Alpine, Calif. 92001

[73] Assignees: W. Keith R. Watson; William W. Haefliger, both of Pasadena, Calif.; part interest to each

[21] Appl. No.: 188,953

[22] Filed: May 2, 1988

Related U.S. Application Data

[63] Continuation-in-part of Ser. No. 828,941, Feb. 12, 1986, which is a continuation of Ser. No. 656,751, Oct. 1, 1984, abandoned, which is a continuation of Ser. No. 426,868, Sep. 29, 1982, abandoned.

[51] Int. Cl.$^4$ .................. A61K 31/10; A61K 31/165; A61K 31/185
[52] U.S. Cl. ................... 514/553; 514/617; 514/708
[58] Field of Search ........ 514/553, 708, 617

*Primary Examiner*—Stanley J. Friedman
*Attorney, Agent, or Firm*—William W. Haefliger

[57] ABSTRACT

A solution of lidocaine hydrochloride, dimethyl sulfoxide and citric acid or citric acid monohydrate is prepared, for topical application to an animal or human.

6 Claims, No Drawings

LIDOCAINE HYDROCHLORIDE, CITRIC ACID AND DIMETHYL SULFOXIDE, SOLUTION, AND FORMATION THEREOF

This application is a C-I-P of Ser. No. 828,941, filed Feb. 12, 1986, which a continuation of Ser. No. 656,751, filed Oct. 1, 1984, which is a continuation of Ser. No. 426,868, filed Sept. 29, 1982, the last two are now abandoned.

BACKGROUND OF THE INVENTION

This invention relates generally to remedial treatments for arthritis, to relieve pain and/or reduce inflammation and deformation or the causes thereof. More particularly, it concerns a composition and method for removing arthritic calcerous deposits.

There exists a long recognized need for techniques or processes which will alleviate arthritic pain and swelling. None of the current remedies, such as the use of pain killers, serves to reduce arthritic calcareous deposits, and reduce or eliminate inflammation without requiring surgery.

SUMMARY OF THE INVENTION

It is a major object of the invention to provide method and composition that will meet the above need. Basically, the method of treating an arthritic zone underlying a skin area, in accordance with the invention, includes the steps:

(a) providing a non-toxic solution that consists essentially of citric acid or other chelate dissolved in dimethyl sulfoxide, the solution containing also lidocaine hydrochloride, (b) and topically applying said solution to the skin area overlying the arthritic zone.

It is found that the solution penetrates the skin and serves to alleviate symptoms of arthritics, such as inflammation, pain and swelling. As will appear, the solution may be applied to a porous pad, to wet same, and the wetted pay may be topically applied at regular intervals to the skin, as at night for as long as necessary to obtain the relief. Several days and in some cases several weeks are required, depending upon the severity of the disease, the skin area being kept wetted by the solution, and wetted pads being replaced at intervals for this purpose. Other body reactive agents are usable.

Other objects of the invention include providing for carriage of the solution as in a porous pad applicable to the skin, and packaging of the wetted pad.

These and other objects and advantages of the invention, as well as the details of an illustrative embodiment, will be more fully understood from the following discussion.

Typically, the pure citric acid is in solid crystalline form and is dissolved in the DMSO, in liquid state. Specifically, 20 to 50 weight percent crystalline powder citric acid is dissolved in 80 to 50 weight percent DMSO, under heating (as by microwave oven at about 140°-200° F.) and agitation (as by stirring) for about 45 to 80 seconds, to produce the solution, which is preferably anhydrous. Crystalline powder lidocaine hydrochloride, in weight percent between 0.4 and 4.0 is also combined into the solution and dissolved with the citric acid powder. Citric acid monohydrate is usable for this purpose, in the same proportions. A specific example is: about 2% lidocaine hydrochloride, about 70% dimethyl sulfoxide, and about 28% of citric acid, the percentages being by weight.

The provision of a porous mechanical carrier for the solution, and application of the solution to the carrier to wet same is done in a conventional manner. For example, the carrier may take the form of a gauze pad on a band with adhesive on band extents for attaching the band to a user's (human or animal) anatomy. The solution may be applied as by droplets from a syringe to saturate the pad. The pad typically is applied to the skin area overlying the arthritic zone, such as a bone or joint. The pad is held in position by the band adhesive areas adherent to the skin. A BAND-AID may serve this purpose.

The saturated pad and band may be enclosed in package such as aluminum foil, with upper and lower layers joined at the edges. This maintains the saturated pad in hermetically sealed condition, for shipment, to prevent moisture contact with the pad prior to use.

In use, the acid-DMSO complex solution containing lidocaine hydrochloride penetrates the skin, subcutaneously, and contacts the arthritic area, characterized by formation of arthritic bone or joint tissue containing calcium phosphate. The citric acid contacts that tissue and reacts therewith to form calcium citrate to be carried away in the blood stream and removed by liver and kidney function.

The reaction is believed to proceed typically as follows:

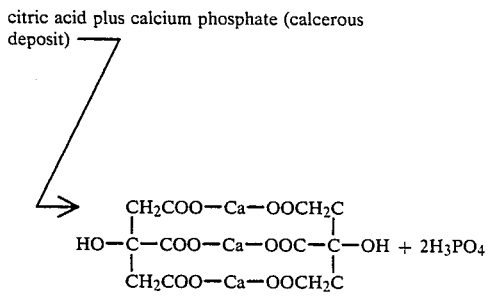

Other reaction products can include "one" calcium citrate, and "two calcium citrate, expressed as follows:

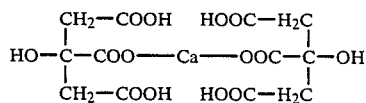

and,

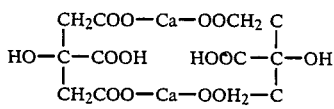

These reaction products are soluble in body fluid such as blood. The treatment is repeated (pad applied) as long as necessary (as at regular intervals, such as during the night) to obtain relief from pain, to reduce or eliminate inflammation, and to reduce swelling and calcerous deposits.

Chelating agents other than citric acid may be employed, and in the same manner as described above for citric acid. Such agents included E.D.T.A.

(ethylenedinitrilo) tetraacetic acid, which complexes heavy metals including calcium, and L-tartaric or M-tartaric acid which reacts with calcium deposits to form calcium tartrate.

The porous mechanical carrier as described may be used to carry other solutions consisting essentially of a body reactive agent dissolved in DMSO; thus, the described technique is usable to replace hypodermic injections, the advantage being that the agent is carried into the bloodstream without requiring skin puncturing. Also, slow administration is achieved. Examples of such agents include insulin, anaesthetics employed as during surgery, acetasalycilic acid (aspirin), procaine and other low molecular weight agents.

As an alternative to the use of gauze pad referred to above, the solution may be dispensed onto the skin from a bottle having a rolling ball, wetted at the side thereof exposed to the bottle contents. As the ball rolls over the skin, the thin layer of solution wetting the ball is transferred to the skin.

I claim:

1. A method for producing a solution useful for treating a human or animal patient afflicted with arthritis to alleviate inflammation, pain and swelling caused by calcium phosphates in bone or joint tissue, by topically applying an effective amount of said solution to the patient's skin surface overlying the inflammed, painful and swollen area of the patient for a period of time sufficient to alleviate said inflammation, pain and swelling, which method comprises:
   (a) providing said solution consisting essentially of a mixture of lidocaine hydrochloride, dimethyl sulfoxide and citric acid or citric acid monohydrate by combining between about 0.4 to 4.0 weight percent of said lidocaine hydrochloride, 20 to 50 weight percent of said citric acid or citric acid monohydrate, and between about 80 to 50 weight percent dimethyl sulfoxide,
   (b) and heating and mixing said citric acid or citric acid monohydrate and dimethyl sulfoxide during the providing of said solution thereof.

2. The method of claim 1 wherein said composition is formed to be anhydrous.

3. The solution prepared by the method of claim 1.

4. The method of claim 1 wherein the mixture consists of:
   about 2.0 weight percent lidocaine hydrochloride,
   about 70.0 weight percent dimethyl sulfoxide,
   about 28 weight percent citric acid.

5. The solution prepared by the method of claim 4.

6. The method of claim 1 wherein the citric acid or citric acid monohydrate, and the lidocaine hydrochdloride, are in crystalline powder form and are dissolved in response to said heating and mixing.

* * * * *